(12) United States Patent
Carinci et al.

(10) Patent No.: US 11,883,147 B2
(45) Date of Patent: Jan. 30, 2024

(54) COMPUTER-IMPLEMENTED MAGNETIC RESONANCE OPERATION

(71) Applicant: Siemens Healthcare GmbH, Erlangen (DE)

(72) Inventors: Flavio Carinci, Würzburg (DE); Mario Zeller, Erlangen (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/840,792

(22) Filed: Jun. 15, 2022

(65) Prior Publication Data

US 2022/0400970 A1 Dec. 22, 2022

(30) Foreign Application Priority Data

Jun. 16, 2021 (EP) .................................. 21179677

(51) Int. Cl.
*G01R 33/48* (2006.01)
*A61B 5/055* (2006.01)
*G01R 33/483* (2006.01)

(52) U.S. Cl.
CPC .......... *A61B 5/055* (2013.01); *G01R 33/4835* (2013.01)

(58) Field of Classification Search
CPC . A61B 5/055; G01R 33/4835; G01R 33/5611
See application file for complete search history.

(56) References Cited

U.S. PATENT DOCUMENTS

| 4,845,430 | A | * | 7/1989 | Nakabayashi | ..... G01R 33/4835 324/309 |
| 5,237,273 | A | * | 8/1993 | Plewes | ............... G01R 33/4835 324/309 |

(Continued)

FOREIGN PATENT DOCUMENTS

EP 3537167 A1 9/2019

OTHER PUBLICATIONS

Barth, Markus et al., "Simultaneous Multislice (SMS) Imaging Techniques: SMS Imaging"; Magnetic Resonance in Medicine., Bd. 75, Nr. 1, Aug. 26, 2015 (Aug. 26, 2015), pp. 63-81, XP055408927, US ISSN: 0740-31; 2015.

(Continued)

*Primary Examiner* — G.M. A Hyder
(74) *Attorney, Agent, or Firm* — Banner & Witcoff Ltd.

(57) ABSTRACT

Method for operating an MR device to acquire MR data slices, wherein in a sequence section of an MR sequence, MR signals of at least two slices are measured simultaneously, and an acquisition order having an association of slices to respective sequence sections of a repetition sequence covering all slices of an associated concatenation is determined using an ordering rule. A crosstalk criterion is evaluated for the acquisition order by checking whether a first slice acquired in a last sequence section of the repetition sequence is directly adjacent to a second slice acquired in a first sequence section of the same repetition sequence. If the crosstalk criterion is fulfilled, the acquisition order is adapted according to an adaptation rule such that a larger temporal acquisition distance between the acquisition of the first and the second slices is provided.

12 Claims, 4 Drawing Sheets

(56) References Cited

U.S. PATENT DOCUMENTS

| | | | | |
|---|---|---|---|---|
| 2010/0289493 | A1* | 11/2010 | Stemmer | G01R 33/5615 |
| | | | | 324/309 |
| 2014/0225612 | A1* | 8/2014 | Polimeni | G01R 33/4835 |
| | | | | 324/309 |
| 2016/0313433 | A1* | 10/2016 | Beck | G01R 33/56509 |
| 2017/0108567 | A1* | 4/2017 | Bhat | G01R 33/5611 |
| 2019/0277930 | A1 | 9/2019 | Paul et al. | |
| 2020/0271741 | A1* | 8/2020 | Paul | G01R 33/4835 |
| 2021/0096199 | A1* | 4/2021 | Koerzdoerfer | G01R 33/565 |

OTHER PUBLICATIONS

Olson, V. Daniel et al.: "Analysis of errors in diffusion kurtosis imaging caused by slice crosstalk in simultaneous multi-slice imaging"; NMR in Biomedicine; vol. 32, No. 11, Aug. 6, 2019 (Aug. 6, 2019), XP055862735; ISSN: 0952-3480, DOI: 10.1002/nbm.4162; URL:https://onlinelibrary.wiley.com/doi/full-xml/10.1002/nbm.4162>.

Setsompop, Kawin et al. "Blipped-Controlled Aliasing in Parallel Imaging for Simultaneous Multislice Echo Planar Imaging With Reduced g-Factor Penalty" Magnetic Resonance in Medicine; vol. 67; No. 5; pp. 1210-1224; DOI 10.1002/mrm.23097.; 2012.

Stemkens B. et al: "Nuts and bolts of 4D-MRI for radiotherapy"; Physics In Medicine And Biology, Institute Of Physics Publishing, Bristol GB; vol. 63, No. 21, Oct. 23, 2018 (Oct. 23, 2018), XP020331420.

\* cited by examiner

COMPUTER-IMPLEMENTED MAGNETIC RESONANCE OPERATION

TECHNICAL FIELD

The disclosure concerns a computer-implemented method for operating a magnetic resonance device to acquire a magnetic resonance data set, which comprises a total number of slices, using a simultaneous multi-slice (SMS) technique, wherein in a sequence section of the used magnetic resonance sequence magnetic resonance signals from a simultaneity number, which is equal to an acceleration factor, of at least two slices are measured simultaneously, wherein an acquisition order comprising an association of slices to respective sequence sections of at least one repetition sequence, wherein the at least one repetition sequence covers all slices of at least one associated concatenation, is determined using at least one ordering rule. The disclosure further concerns a magnetic resonance device, a computer program and an electronically readable storage medium.

BACKGROUND

Magnetic resonance imaging is an established imaging modality, in particular in medicine. Improvement activity is mostly directed to the image quality, but also to the reduction of the, partly very long, acquisition times. One of the key elements to optimize acquisition times is the parallel acquisition of multiple slices.

In particular, the simultaneous multi-slice technique (SMS technique) has been proposed to accelerate magnetic resonance imaging. Here, a number of slices given by an acceleration factor, for example two or three, are at least essentially simultaneously excited and simultaneously read out. SMS techniques are, for example, described in the preview article by Markus Barth et al., "Simultaneous Multi Slice (SMS) Imaging Techniques", Magn Reson Med 75 (2016), pages 63-81. In other words, the at least essentially simultaneously excited slices are "collapsed" into one image, that is, the magnetic resonance signal measure comprises information from all these slices. The magnetic resonance data of the simultaneously measured slices can be separated in post-processing utilising separation algorithms like, for example, slice GRAPPA (see, for example, the article by K. Setsompop et al., "Blipped-Controlled Aliasing in Parallel Imaging (blipped-CAIPI) for simultaneous multi-slice EPI with reduced g-factor penalty", Magn. Reson. Med. 67 (2012), pages 1210-1224.

One known problem in SMS imaging is the so-called slice crosstalk. When a slice is excited, the longitudinal magnetisation in the neighbouring slices is also partially saturated. The reason for this effect is that the slice excitation profile is not a perfect rectangular function and overlaps with the adjacent slices. To overcome this problem, it was proposed to choose the acquisition order in time for the slices such that slice excitations are interleaved, meaning that neighbouring slices are not excited directly after each other in time, but a time delay is allowed by the acquisition order (which may also be called reordering scheme) itself. If, for example, a total number of twelve slices are numbered according to the spatial arrangement, in an acquisition order of S1 S2 S3 S4 S5 S6 S7 S8 S9 S10 S11 S12, slice crosstalk would occur. If, however, an acquisition order interleaved in time like S1 S3 S5 S7 S9 S11 S2 S4 S6 S8 S10 S12 is used, slices which are close in space such as S1 and S2 are never excited one after each other. In SMS imaging, however, the interleaved slice reordering does not always succeed in avoiding slice crosstalk, due to the simultaneous excitation of slices which are at different locations in space. In the example above, using an acceleration factor of two, the following pairs of slices would be excited simultaneously: (S1,S7), (S2,S8), (S3,S9), (S4,S10), (S5,S11), (S6,S12). Using the interleaved reordering scheme, the following acquisition order (and thus excitation order) in time results: (S1,S7), (S3,S9), (S5,S11), (S2,S8), (S4,S10), (S6,S12).

Since often multiple repetitions of a repetition sequence are used for acquisition, after ending one repetition with slices S6 and S12, the next repetition would start with slices S1 and S7, such that slices S6 and S7, which are adjacent in space are excited directly after each other. Slice S6 is excited in the last sequence section of the first repetition of the repetition sequence and slice S7 is excited in the first sequence section of the second repetition of the repetition sequence. This may cause slice crosstalk, which results in an artifact in the final magnetic resonance data set. In the described example, slice S7 would appear darker than all other slices because its magnetization has been partially saturated by the excitation of slice S6, which is acquired directly before it.

SUMMARY

It is an object of the current disclosure to improve image quality in SMS imaging, in particular regarding the reduction of slice crosstalk artifacts.

According to the disclosure, this object is achieved by providing a computer-implemented method, a magnetic resonance device, a computer program and an electronically readable storage medium.

In a method as initially described, according to the disclosure, a crosstalk criterion is evaluated for the determined acquisition order, wherein the crosstalk criterion checks whether at least one first slice acquired at the end of at least one of the at least one repetition sequence, in particular in the last sequence section of at least one of the at least repetition sequence, is spatially adjacent, in particular directly adjacent, to at least one second slice acquired at the beginning of the same repetition sequence, in particular in the first sequence section of the same repetition sequence, and, if the crosstalk criterium is fulfilled, the acquisition order is adapted according to at least one adaption rule such that a larger temporal acquisition distance between the acquisition of the first and the second slice is provided, in particular for the affected repetition sequence.

Hence, thereafter, the magnetic resonance data set may be acquired using the, possibly adapted, acquisition order.

In the method according to the disclosure, known ordering rules are applied as usual to determine an acquisition order for the total number of slices, the acceleration factor and the concatenation number, which may be one, but often is more than one. Multiple concatenations are, for example, used if not all sequence sections for all slices fit into one repetition time (TR), so that they are distributed to more than one concatenation and respective repetition sequences. Of course, if multiple concatenations are used, there are multiple different repetition sequences, wherein an acquisition order for each concatenation and hence each repetition sequence is determined. In this case, of course, the adaptation concerns at least the repetition sequence for which the crosstalk criterion is fulfilled, which is, usually, the concatenation having the most slices, as will be further explained using the examples described below.

Preferably, as known from the art, the total number modulo the acceleration factor equals zero. That is, the slices can be evenly distributed to slice groups associated with sequence sections of the at least one repetition sequence.

Once the acquisition order is determined using the ordering rules, as principally known, the method according to the disclosure evaluates a crosstalk criterion which, in essence, checks if slice crosstalk may occur if a repetition sequence is repeated multiple times. The crosstalk criterion is fulfilled if two spatially adjacent, in particular spatially directly adjacent, slices, namely the first and the second slice, exist at the end and the beginning of the repetition sequence, respectively, which are not far enough separated in time to exclude relevant crosstalk, which would lead to image artifacts. In most of the cases, relevancy can be assumed if spatially directly adjacent first and second slices are acquired (and thus excited) in two temporally directly adjacent sequence sections. Hence, the crosstalk criterion is in particular fulfilled if a first slice acquired in the last sequence section of the repetition sequence and a second slice acquired in the first sequence section of the same repetition sequence are directly adjacent in space.

It is noted that the crosstalk criterion does, in many cases, not have to explicitly evaluate the determined acquisition order, as it can be formulated as a simpler mathematical relation for common ordering rules and their result, as will be further explained below. In particular, the crosstalk criterion may check whether a mathematical relation depending on the total number, the acceleration factor and the concatenation number is true. This simplifies implementation and reduces computing time.

If the crosstalk criterion is fulfilled, that is, slice crosstalk is to be expected, the acquisition order is adapted according to at least one adaptation rule such that a larger temporal acquisition distance between the acquisition of the first and the second slice is provided for the affected repetition sequence or even different repetition sequences, without having two other, spatially adjacent, in particular directly spatially adjacent, slices being acquired adjacent, in particular directly adjacent, in time. That is, of course, applying the adaptation rule should not lead to slice crosstalk elsewhere in the affected repetition sequence or another repetition sequence of another concatenation. This can be seen as a boundary condition which, however, can be implicitly fulfilled if the at least one ordering rule is considered when defining the at least one adaptation rule.

In preferred, general aspects, the acquisition order may be adapted by, as the at least one adaptation rule, exchanging at least the first or second slice acquired in an affected sequence section with at least one further slice in a further sequence section in the affected repetition sequence, in particular regarding the next to last and the last sequence sections or the second and first sequence sections of the affected repetition sequence, or with at least one further slice in another repetition sequence. For example, as such a modification to a conventional (interleaved) slice reordering scheme, the slices associated with the last sequence section in the repetition sequence may be exchanged with the slices associated with the second to last sequence section. However, aspects, in which the slices associated with the last sequence section in the repetition sequence may also be exchanged with the slices of any other sequence section within the same concatenation, except the first sequence section in the repetition sequence. Of course, the adaptation rule may also only exchange single slices, that is, exchange the first slice from its current sequence section with another slice in the repetition sequence, except, of course, the second slice. It is noted that this exchange is also possible across concatenations. Of course, these possibilities, as explained for the end of the repetition sequence, may also be applied to the beginning of the repetition sequence, that is, the second slice and its sequence section.

For clarity, it should be noted that the adaptation is, of course, performed for each time the repetition sequence is repeated.

In summary, the current disclosure allows to automatically change the acquisition order of slices in SMS imaging if the combination of total number of slices, acceleration factor, and concatenation number would lead to slice crosstalk using known ordering rules. Hence, improved image quality with reduced slice crosstalk artifacts results.

In an often used example, if the slices are numbered according to the spatial arrangement in at least one stacking direction and a concatenation number of concatenations is used, the ordering rule may define simultaneous acquisition of multiple slices of slice groups such that the slice numbers of slices in each slice group differ by the total number divided by the acceleration factor, such that a list of slice groups sorted in an ascending or descending manner according to their lowest slice number results, wherein, to distribute the slice groups to concatenations and to the sequence sections, if the concatenation number is 1, two sublists are scheduled one after the other, one sublist containing all even slice numbers, the other the uneven slice numbers, and if the concatenation number is greater than 1, slice groups according to the list are successively assigned to different concatenations in a defined concatenation order.

It is noted that, using these ordering rules, if the same number of slices is acquired in each concatenation, the crosstalk criterion will not be fulfilled in any case; however, it will, if these ordering rules are used, always be fulfilled for one concatenation.

For example, if a total number of 26 slices are acquired using an acceleration factor of two and a concatenation number of three concatenations, the repetition sequences for each concatenation would include the following slice groups in temporal order:

Concatenation 1: (S1,S14), (S4,S17), (S7,S20), (S10, S23), (S13,S26)
Concatenation 2: (S2,S25), (S5,S18), (S8,S21), (S11,S24)
Concatenation 3: (S4,S16), (S6,S19), (S9,S22), (S12, S25).

As can be seen, the last sequence section in the repetition sequence for concatenation 1 includes slice S13, while the first sequence section comprises slice S14. Hence, when the repetition is repeated, spatially directly adjacent slices S13 and S14 are acquired (and thus excited) directly adjacent in time. A comparable slice crosstalk risk results for example for a total number of 39 slices, an acceleration factor of three and a concatenation number of two; for the total number of slices of 38, an acceleration factor of two and a concatenation number of two; for a total number of slices of 39, an acceleration factor of three and a concatenation number of three.

Using these ordering rules, the inventors have found that slice crosstalk occurs if a simple mathematical relation is true. In particular, in preferred aspects, to evaluate the crosstalk criterion, wherein the reduced number of slices is defined as the total number of slices divided by the acceleration factor, it is checked whether a first integer, defined as the reduced number of slices, modulo a second integer, defined as the concatenation number, equals one.

That is, in this often used ordering scheme, the mentioned slice crosstalk problem occurs only with special combinations of the total number of slices (NTotalSlices), the SMS acceleration factor (SMSfactor) and the concatenation number (NConcatenations). These combinations are defined by the following logic mathematical relation being fulfilled:

NReducedSlices+% NConcatenations==1, wherein:
the symbol % represents a modulo operation, and
NReducedSlices=NTotalSlices/SMSfactor.

All these variables above are integers, which are greater than zero.

To evaluate the crosstalk criterion, in this aspect, it is checked whether the current combination of the total number of slices (NTotalSlices), the acceleration factor (SMSfactor), and the concatenation number (NConcatenations) would lead to slice crosstalk by checking whether the logic mathematic relation described above, NReducedSlices % NConcatenations==1, is true. If so, the at least one adaptation rule is applied.

Preferably, in this aspect, the acquisition order may be adapted by an adaptation rule, according to which, in the repetition sequence of the concatenation comprising the most slices, the association of the last two slice groups or the first two slice groups to their respective sequence sections is exchanged. However, alternatively, it is also possible to exchange the slices of the first or last sequence section with the slices of any other sequence section of the repetition sequence (except the first or last sequence section, of course). Furthermore, it is conceivable to exchange only the first or second slice with another slice not being the first or second slice, in particular in any repetition sequence of any concatenation, as already discussed above.

The disclosure further concerns a magnetic resonance device, comprising a control device adapted to perform the steps of a method according to the disclosure. All remarks and features regarding the method according to the disclosure may be analogously applied to the magnetic resonance device according to the disclosure, such that the same advantages are achieved.

In particular, the control device may comprise at least one processor and at least one storage means. Functional units for performing steps of the method according to the disclosure can be implemented by hardware and/or software. In particular, the control device may comprise an ordering unit for applying the at least one ordering rule to determine the acquisition order, a criterion unit for evaluating the crosstalk criterion, and an adaptation unit for adapting the acquisition order according to the at least one adaptation rule if the crosstalk criterion is fulfilled. For finally acquiring the magnetic resonance data set, the control device may, as in principle known, also comprise a sequence unit.

A computer program according to the disclosure can be directly loaded into a storage means of a control device of a magnetic resonance device and comprises program means to perform the steps of a method according to the disclosure if the computer program is executed in the control device of the magnetic resonance device. The computer program may be stored on an electronically readable storage medium according to the disclosure, which hence comprises control information comprising a computer program according to the disclosure, such that, when the storage medium is used in a control device of a magnetic resonance device, the control device is controlled to perform the steps of a method according to the disclosure. In particular, the storage medium may be a non-transitory storage medium, for example a CD-ROM.

BRIEF DESCRIPTION OF THE DRAWINGS

Other objects and features of the present disclosure will become apparent from the following detailed description considered in conjunction with the accompanying drawings. The drawings, however, are only principal sketches designed solely for the purpose of illustration and do not limit the disclosure. The drawings show.

DETAILED DESCRIPTION

Figure 1:
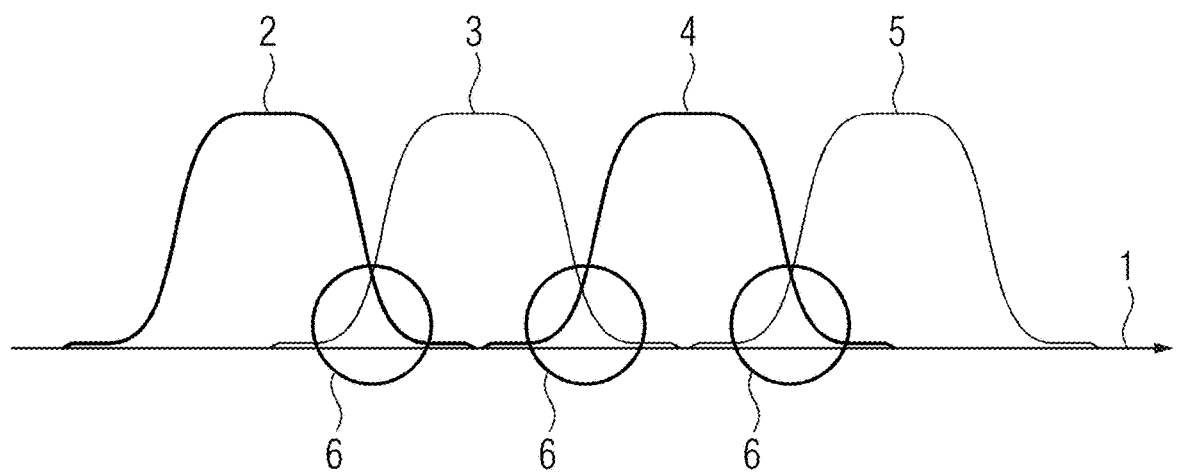
FIG. 1 excitation profiles of adjacent slices,
FIG. 2 a schematical illustration of a slice crosstalk artifact,
FIG. 3 a flowchart of an aspect of a method according to the disclosure,
FIG. 4 a repeated repetition sequence of an acquisition order before adaptation,
FIG. 5 the repeated repetition sequence after adaptation,
FIG. 6 a magnetic resonance device according to the disclosure, and
FIG. 7 the functional structure of a control device of the magnetic resonance device.

FIG. 1 schematically illustrates the problem of crosstalk of spatially adjacent slices in a stacking direction 1 by showing excitation profiles 2, 3, 4 and 5. As can be seen, these excitation profiles 2 to 5 are not perfectly rectangular, such that they overlap into the area of neighbouring slices in crosstalk regions 6. Hence, when acquiring magnetic resonance data from multiple slices in a slice stack, temporally adjacent excitation of spatially directly adjacent slices is avoided, for example by interleaving, as already described above.

Figure 2:
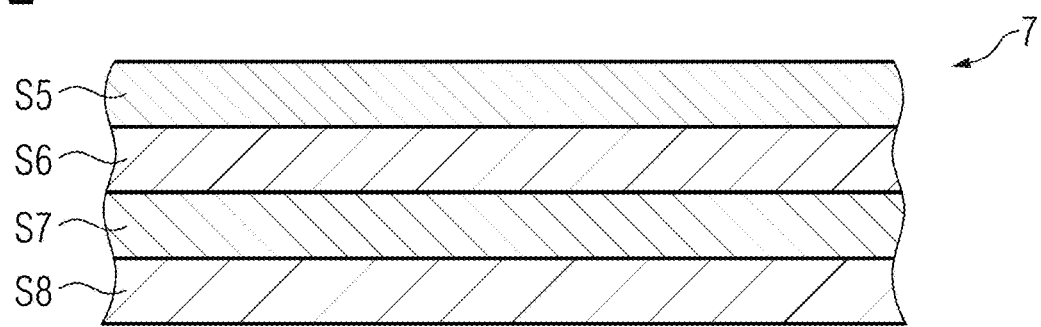

The crosstalk problem may also occur in simultaneous multi-slice imaging (SMS imaging), even if an ordering scheme, described by at least one ordering rule, according to the state of the art is employed to determine an acquisition order. If, for example, a total number of twelve slices S1 to S12 in one concatenation is to be acquired, known ordering rules, for example as described above, using an acceleration factor of two, lead to the following slice groups in temporal order, as assigned to sequence sections the repetition sequence of the, in this case one, concatenation: (S1,S7), (S3,S9), (S5,S11), (S2,S8), (S4,S10), (S6,S12). Since the repetition sequence is repeated multiple times, (S6,S12) and (S1,S7) are acquired directly adjacent in time, such that a saturation of the magnetisation in slice S7 remains from the previous excitation of slice S6. In consequence, as indicated in FIG. 2, showing schematically slices S5, S6, S7, and S8 of a magnetic resonance data set 7, the slice S7 is darker than all the other slices.

Figure 3:
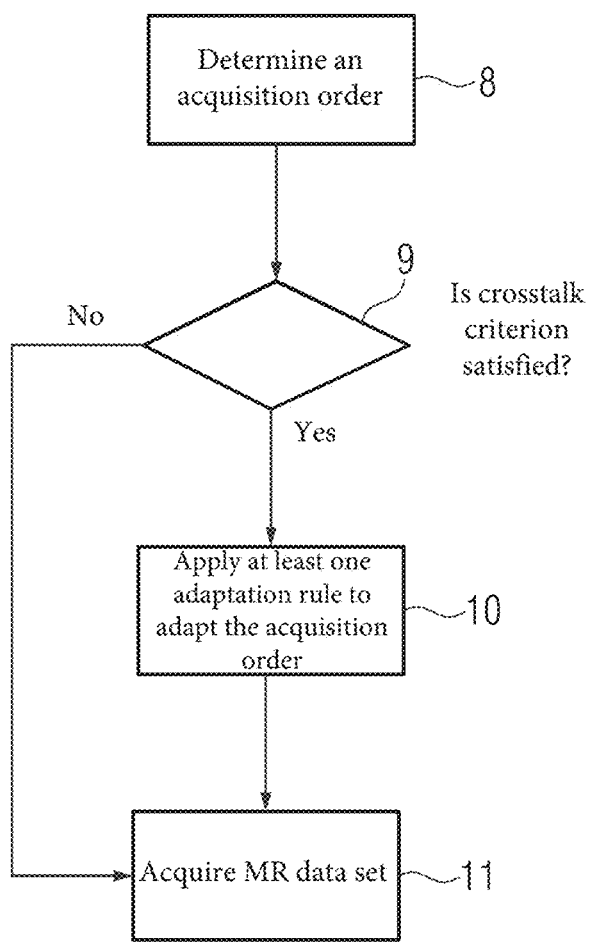

According to a method described in FIG. 3, such crosstalk artifacts may be prevented. In a first step 8 of FIG. 3, the acquisition order is determined as known from the state of the art by applying ordering rules, for example such that, as explained above, slices numbered according to the spatial arrangement in at least one stacking direction are sorted into slice groups, such that the slice numbers of slices in slice groups differs by the total number of slices divided by the acceleration factor. As a result, a list of slice groups sorted in ascending or descending manner according to the lowest slice number is determined. These slice groups are now associated with concatenations and with sequence sections of the repetition sequences of the corresponding concatenations by, in the case that only one concatenation (and hence one repetition sequence) is defined, scheduling two sublists one after the other, one sub list containing all even slice numbers, the other sublist the uneven slice numbers as explained above in the twelve slices example. However, in most practical cases, more than one concatenation is used, wherein slice groups according to the list are successively assigned to different concatenations in a defined concatenation order. For example, if the concatenation order is C1, C2, C3, the first slice group according to the list is assigned to C1, the second to C2, the third to C3, the fourth to C1, the fifth to C2, and so on. In the example already discussed above, the following repetitions result for a total number of slices of 26, an acceleration factor of two and a concatenation number of three.

C1: (S1,S14), (S4,S17), (S7,S20), (S10,S23), (S13,S26)
C2: (S2,S15), (S5,S18), (S8,S21), (S11,S24)
C3: (S3,S16), (S6,S19), (S9,S22), (S12,S25).

In a step 9, a crosstalk criterion is evaluated for the determined acquisition order. The crosstalk criterion checks whether at least one first slice acquired in the last sequence section of one of the repetition sequences is spatially directly adjacent to at least one second slice acquired in the first sequence section of the same repetition sequence, such that, upon repeating the repetition sequence, the first and the second slice would be acquired (and thus excited) temporally directly adjacent. In the example above, in the repetition for C1, the first slice would be slice S13, the second slice would be slice S14.

However, in this aspect, the crosstalk criterion does not analyse the repetition sequences themselves, but checks whether a logic mathematical relation depending on the total number of slices, the acceleration factor and the concatenation number is fulfilled. Using the ordering scheme as exemplarily described above with respect to step 8, the mathematical relation is that a first integer, defined as a reduced number of slices, modulo a second integer, defined as the concatenation number, should be equal to one. Here, the reduced number of slices is defined as the total number of slices divided by the acceleration factor.

If it is determined in step 9 that the crosstalk criterion is fulfilled, that is, the mathematical relation is true, the acquisition order is adapted in step 10, else imaging begins with the originally determined acquisition order of step 8 in step 11.

In step 10, at least one adaptation rule is applied to adapt the acquisition order such that a larger temporal acquisition distance between the first and the second slice is provided for the affected repetition sequence without having two other, spatially directly adjacent slices being acquired directly adjacent in time. In the example already discussed with respect to step 8 and step 9, the affected repetition sequence will always be the one associated with the concatenation having the most slices. In this aspect, the adaptation rule describes exchanging the slices to be acquired in the last sequence segment of the affected acquisition with the slices acquired in the second to last sequence segment of the affected repetition.

Figure 4:
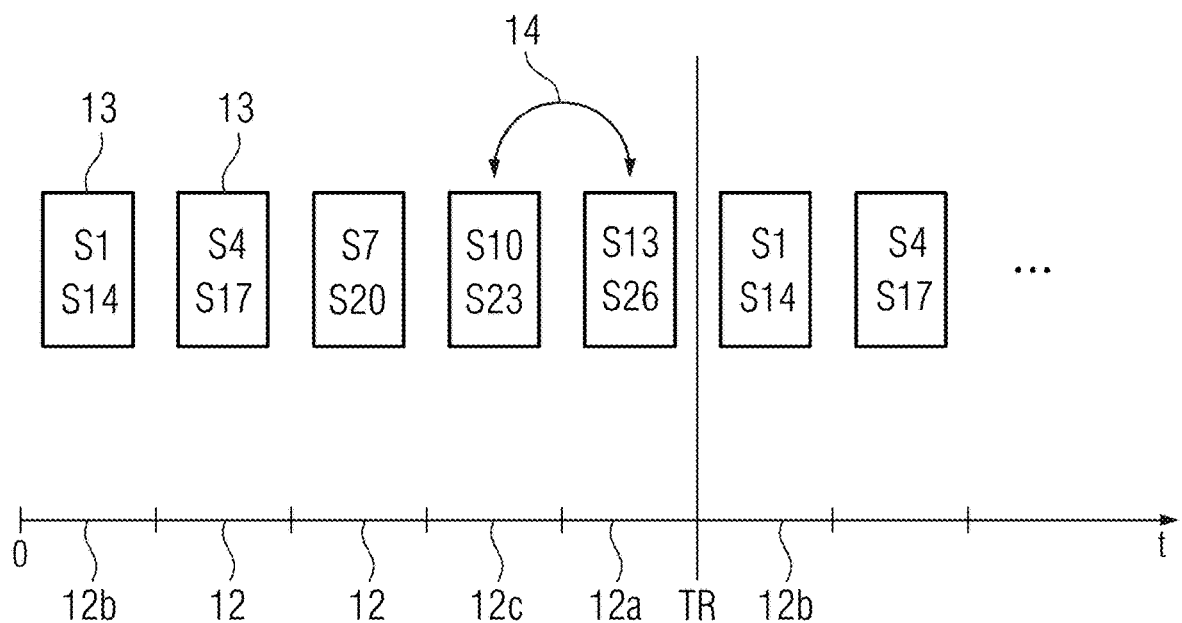
Figure 5:
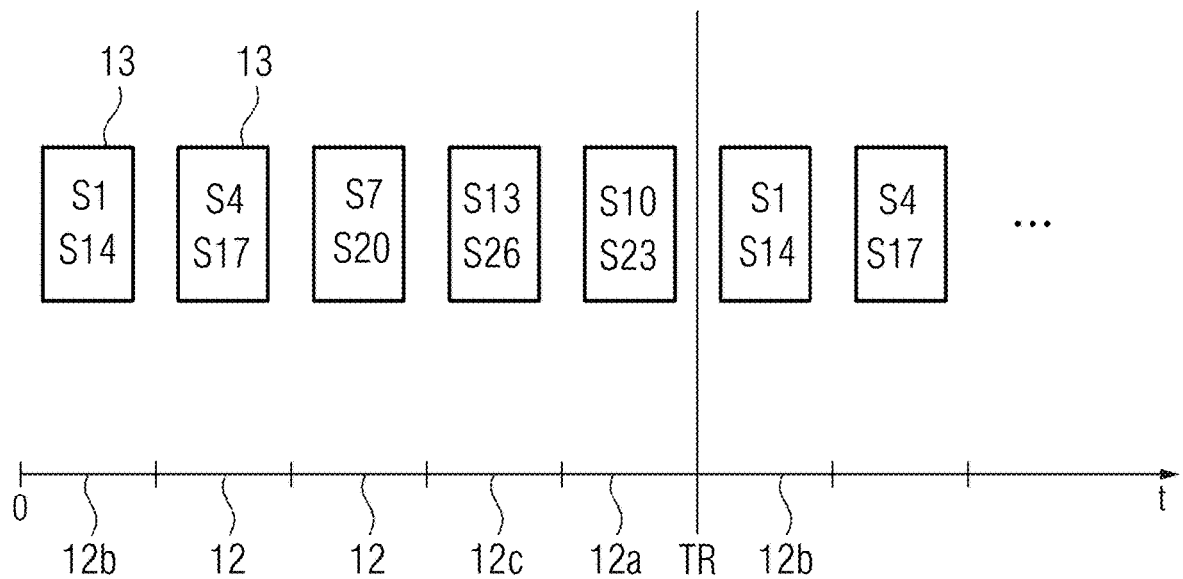

This is exemplarily shown in FIGS. 4 and 5 for the repetition C1 discussed above. As can be seen in FIG. 4, according to the acquisition order determined in step 8, the repetition sequence for one repetition time TR is divided into sequence segments 12, to which respective slice groups 13 have been assigned. In the last sequence section 12a, slices S13 and S26 are measured, while in the first sequence section 12b, temporally directly adjacent to the last sequence section 12a since the repetition sequence is repeated, slices S1 and S14 are acquired. This leads to slice crosstalk in slice S14. To adapt the acquisition order, as indicated by arrow 14 in FIG. 4, the slice groups 13 associated with the last sequence section 12a and the next to last sequence section 12c are exchanged, such that, as shown in FIGS. 5, S13 and S26 are now acquired in sequence section 12c, while S10 and S23 are now acquired in sequence section 12a, such that the temporal distance between the acquisition of slices S13 and S14 has been increased.

It is, however, noted that other adaptation rules may also be applied, for example only exchanging S10 and S13 in sequence sections 12a and 12c or even exchanging to other slices/other slice groups 13 further away than segment section 12c. Of course, it is also possible to change the position in time regarding S14 analogously.

In step 11, the magnetic resonance data set is acquired using the acquisition order.

Figure 6:
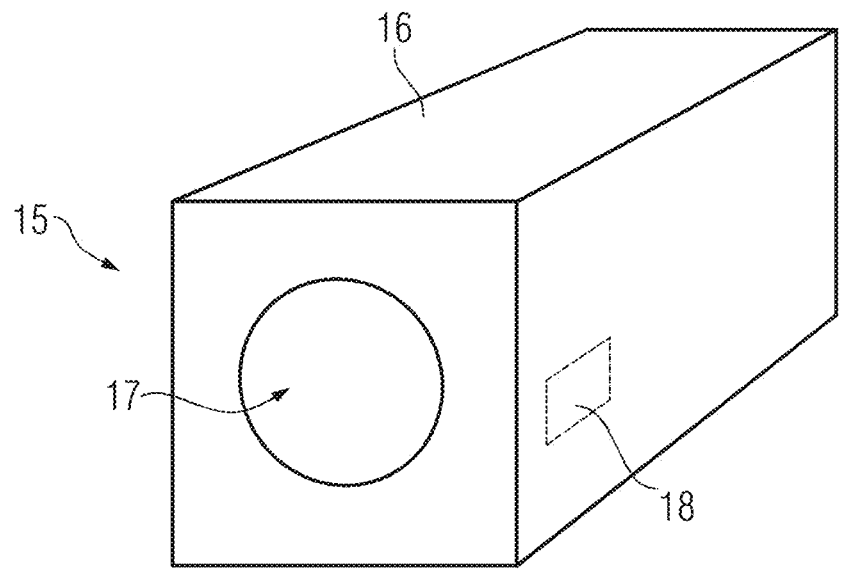

FIG. 6 is a principle view of a magnetic resonance device 15 according to the disclosure. The magnetic resonance device 15 comprises, as known from the art, a main magnet unit 16 having a cylindrical bore 17 for receiving a patient on a patient table (not shown). Surrounding the bore, a high frequency coil arrangement and a gradient coil arrangement may be provided. The operation of the magnetic resonance device 15 is controlled by control device 18.

Figure 7:
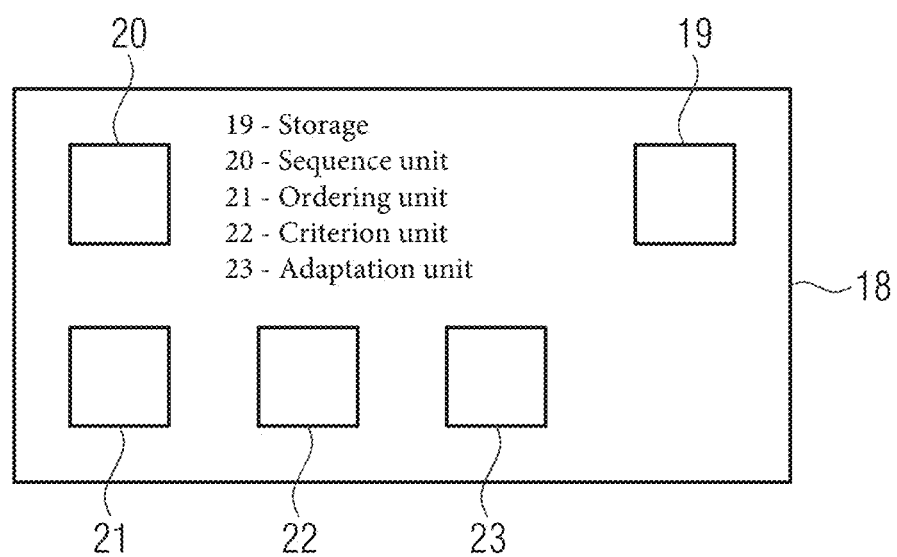

FIG. 7 shows the functional structure of control device 18. Control device 18 comprises a storage means 19 in which, for example, the at least one ordering rule, the at least one adaptation rule and the crosstalk criterion can be stored as well as other data regarding the method according to the disclosure or generally the operation of the magnetic resonance device 15. In particular, the control device 18 comprises a sequence unit 20 for controlling the acquisition of magnetic resonance data, for example according to step 11.

In an ordering unit 21, the acquisition order can be determined according to step 8. The control device 18 further comprises a criterion unit 22 for evaluating the crosstalk criterion (step 9) and an adaptation unit 23 for performing step 11.

Although the present disclosure has been described in detail with reference to the preferred aspect, the present disclosure is not limited by the disclosed examples from which the skilled person is able to derive other variations without departing from the scope of the disclosure.

The invention claimed is:
1. A computer-implemented method for operating a magnetic resonance device, comprising:
  acquiring, using a simultaneous multi-slice technique, a magnetic resonance data set having a total number of slices;
  in a sequence section of a magnetic resonance sequence, simultaneously measuring slices associated with magnetic resonance signals using a simultaneity number that is equal to an acceleration factor of at least two;
  determining an acquisition order having an association of slices to respective sequence sections of at least one repetition sequence covering all slices of at least one associated concatenation using at least one ordering rule;
  evaluating a crosstalk criterion for the determined acquisition order by checking whether a first slice acquired in a last sequence section of at least one of the at least one repetition sequence is directly adjacent to a second slice acquired in a first sequence section of the same repetition sequence; and if the crosstalk criterion is fulfilled, adapting the acquisition order according to at least one adaptation rule to provide a larger temporal acquisition distance between the acquisition of the first slice and the second slice.

2. The computer-implemented method according to claim 1, wherein the acquisition order is adapted by exchanging the first or second slice acquired in an affected sequence section with a further slice in a further sequence section adjacent to the affected sequence section.

3. The computer-implemented method according to claim 1, wherein:
the slices are numbered according to their spatial arrangement in at least one stacking direction and a concatenation number of concatenations is used,
the ordering rule defines simultaneous acquisitions of multiple slices of slice groups such that slice numbers of slices in each slice group differs by a total number divided by the acceleration factor such that a list of slice groups is sorted in ascending or descending manner according to their lowest slice number results to distribute the slice groups to concatenations and to sequence sections, and further comprising:
if the concatenation number is one, two sublists are scheduled one after the other, with one sublist including all even slice numbers, and another sublist including odd slice numbers, and
if the concatenation number is greater than one, slice groups according to the list are successively assigned to different concatenations in a defined concatenation order.

4. The computer-implemented method according to claim 3, wherein in evaluating the crosstalk criterion, a reduced number of slices is defined as the total number divided by the acceleration factor, and
wherein the evaluating comprises checking whether a first integer, defined as the reduced number of slices, modulo a second integer, defined as the concatenation number, equals one.

5. The computer-implemented method according to claim 3, wherein the acquisition order in the repetition sequence of the concatenation having the most slices is adapted by exchanging the association of a last two slice groups or a first two slice groups of the respective sequence sections.

6. The computer-implemented method according to claim 1, wherein:
the slices are numbered according to their spatial arrangement in at least one stacking direction and a concatenation number of concatenations is used,
in evaluating the crosstalk criterion, a reduced number of slices is defined as a total number divided by the acceleration factor, and
the evaluating comprises checking whether a first integer, defined as the reduced number of slices, modulo a second integer, defined as the concatenation number, equals one.

7. The computer-implemented method according to claim 1, wherein the slices are numbered according to their spatial arrangement in at least one stacking direction and a concatenation number of concatenations is used, and
wherein the acquisition order in the repetition sequence of the concatenation having the most slices is adapted by exchanging the association of a last two slice groups or a first two slice groups of the respective sequence sections.

8. The computer-implemented method according to claim 1, wherein:
the slices are numbered according to their spatial arrangement in at least one stacking direction and a concatenation number of concatenations is used, and
the ordering rule defines simultaneous acquisitions of multiple slices of slice groups such that slice numbers of slices in each slice group differs by a total number divided by the acceleration factor such that a list of slice groups is sorted in ascending or descending manner according to their lowest slice number results to distribute the slice groups to concatenations and to sequence sections.

9. The computer-implemented method according to claim 8, further comprising:
if the concatenation number is one, two sublists are scheduled one after the other, with one sublist including all even slice numbers, and another sublist including odd slice numbers.

10. The computer-implemented method according to claim 8, further comprising:
if the concatenation number is greater than one, slice groups according to the list are successively assigned to different concatenations in a defined concatenation order.

11. A magnetic resonance device, comprising:
a main magnet; and
a control device adapted configured to:
acquire, using a simultaneous multi-slice technique, a magnetic resonance data set having a total number of slices;
in a sequence section of a magnetic resonance sequence, simultaneously measure slices associated with magnetic resonance signals using a simultaneity number that is equal to an acceleration factor of at least two;
determine an acquisition order having an association of slices to respective sequence sections of at least one repetition sequence covering all slices of at least one associated concatenation using at least one ordering rule;
evaluate a crosstalk criterion for the determined acquisition order by checking whether a first slice acquired in a last sequence section of at least one of the at least one repetition sequence is directly adjacent to a second slice acquired in a first sequence section of the same repetition sequence; and
if the crosstalk criterion is fulfilled, adapting the acquisition order according to at least one adaptation rule to provide a larger temporal acquisition distance between the acquisition of the first slice and the second slice.

12. A non-transitory electronically-readable storage medium including a computer program that, when executed on a control device of a magnetic resonance device, causes the magnetic resonance device to:
acquire, using a simultaneous multi-slice technique, a magnetic resonance data set having a total number of slices;
in a sequence section of a magnetic resonance sequence, simultaneously measure slices associated with magnetic resonance signals using a simultaneity number that is equal to an acceleration factor of at least two;
determine an acquisition order having an association of slices to respective sequence sections of at least one repetition sequence covering all slices of at least one associated concatenation using at least one ordering rule;

evaluate a crosstalk criterion for the determined acquisition order by checking whether a first slice acquired in a last sequence section of at least one of the at least one repetition sequence is directly adjacent to a second slice acquired in a first sequence section of the same repetition sequence; and if the crosstalk criterion is fulfilled, adapting the acquisition order according to at least one adaptation rule to provide a larger temporal acquisition distance between the acquisition of the first slice and the second slice.

* * * * *